(12) United States Patent
Wang et al.

(10) Patent No.: US 9,150,982 B2
(45) Date of Patent: Oct. 6, 2015

(54) CRYSTAL FORM OF (6S)-5-METHYLTETRAHYDROFOLATE SALT AND METHOD FOR PREPARING SAME

(71) Applicant: LIANYUNGANG JINKANG HEXIN PHARMACEUTICAL CO. LTD., Jiangsu (CN)

(72) Inventors: Zheqing Wang, East Haven, CT (US); Yongzhi Cheng, Jiangsu (CN); Heng Huang, Jiangsu (CN); Huizhen Li, Jiangsu (CN)

(73) Assignee: LIANYUNGANG JINKANG HEXIN PHARMACEUTICAL CO. LTD., Jiangsu (CN)

( * ) Notice: Subject to any disclaimer, the term of this patent is extended or adjusted under 35 U.S.C. 154(b) by 0 days.

(21) Appl. No.: 14/373,262

(22) PCT Filed: Dec. 17, 2012

(86) PCT No.: PCT/CN2012/086794
§ 371 (c)(1),
(2) Date: Jul. 18, 2014

(87) PCT Pub. No.: WO2013/107236
PCT Pub. Date: Jul. 25, 2013

(65) Prior Publication Data
US 2015/0018357 A1  Jan. 15, 2015

(30) Foreign Application Priority Data

Jan. 20, 2012 (CN) .......................... 2012 1 0018941
Jan. 20, 2012 (CN) .......................... 2012 1 0019038
Apr. 25, 2012 (CN) .......................... 2012 1 0125133

(51) Int. Cl.
| C07D 475/04 | (2006.01) |
| C30B 30/06 | (2006.01) |
| A23L 1/30 | (2006.01) |
| A61K 31/519 | (2006.01) |
| C30B 7/14 | (2006.01) |
| C30B 29/54 | (2006.01) |
| A23L 1/303 | (2006.01) |

(52) U.S. Cl.
CPC . *C30B 30/06* (2013.01); *A23L 1/30* (2013.01); *A23L 1/303* (2013.01); *A61K 31/519* (2013.01); *C07D 475/04* (2013.01); *C30B 7/14* (2013.01); *C30B 29/54* (2013.01); *A23V 2002/00* (2013.01); *C07B 2200/13* (2013.01)

(58) Field of Classification Search
CPC .................................................... C07D 475/04
See application file for complete search history.

(56) References Cited

U.S. PATENT DOCUMENTS

| 5,223,500 A | 6/1993 | Gennari |
| 6,441,168 B1 * | 8/2002 | Muller et al. ................. 544/258 |

FOREIGN PATENT DOCUMENTS

| CN | 1277197 A | 12/2000 |
| CN | 1765898 A | 5/2006 |
| CN | 102584826 A | 7/2012 |
| CN | 102702200 A | 10/2012 |
| CN | 102775407 A | 11/2012 |
| WO | 2008/144953 A1 | 12/2008 |

OTHER PUBLICATIONS

International Search Report for corresponding International Application No. PCT/CN2012/086794, mailed Mar. 28, 2013 (4 pages).
International Preliminary Report for corresponding International Application No. PCT/CN2012/086794, mailed May 5, 2014 (8 pages).

* cited by examiner

*Primary Examiner* — Bruck Kifle
(74) *Attorney, Agent, or Firm* — Osha Liang LLP

(57) ABSTRACT

Disclosed are a crystal form of (6S)-5-methyltetrahydrofolate salt and a method for preparing the same. The crystal form is: Form C of the crystal form of (6S)-5-methyltetrahydrofolate calcium salt, where the X-ray diffraction pattern has diffraction peaks at the 2θ angles of 6.3±0.2 and 19.2±0.2; or the crystal form of (6S)-5-methyltetrahydrofolate strontium salt, where the X-ray diffraction pattern has diffraction peaks at the 2θ angles of 6.5±0.2 and 22.0±0.2. The crystal form of (6S)-5-methyltetrahydrofolate salt of the present invention has the advantages of excellent physicochemical properties, good stability, high purity, good reproducibility, and being more suitable for production on an industrial scale.

8 Claims, 2 Drawing Sheets

CRYSTAL FORM OF (6S)-5-METHYLTETRAHYDROFOLATE SALT AND METHOD FOR PREPARING SAME

BACKGROUND

1. Technical Field

The present invention belongs to the field of crystal forms of compounds, and specifically relates to a crystal form of (6S)-5-methyltetrahydrofolate salt and methods for preparing the same and uses of the same.

2. Related Art

The crystal forms of active pharmaceutical ingredients are closely associated with the biological activity, bioavailability, dissolution, stability, and shelf life thereof. Therefore, during the research and development of new drugs, screening of crystal form is one of the most important tasks. Even if the drug has been on the market for many years, seeking more effective crystal forms of the drug is still the goal intensely pursued by pharmaceutical companies.

5-methyltetrahydrofolic acid was first separated from a horse liver in the form of barium salt by Donaldson et al. in 1959 and was named as Prefolic-A, and was synthesized by a chemical method in 1961 (K. O. Donaldson et al., Fed. Proc, (1961), 20, 453).

The 5-methyltetrahydrofolic acid molecule has two chiral carbon atoms, where the configuration of the chiral carbon atom at the glutamic acid site is certain, while the chiral carbon atom at Site 6 has two configurations R and S, and therefore, 5-methyltetrahydrofolic acid has been used in the form of a diastereomeric mixture. It is reported that, the two isomers have different effects with in vivo enzymes, where the compound with S configuration of the carbon atom at site 6 exhibits good efficacy, while the compound with R configuration of the carbon atom at site 6 almost has no efficacy in comparison.

The chemical name of (6S)-5-methyltetrahydrofolic acid is (6S)—N[4-[[(2-amino-1,4,5,6,7,8-hexahydro-4-oxo-5-methyl-6-pteridinyl)methyl]amino]benzoyl]-L-glutamic acid, referred to as (6S)-5-MTHF for short hereinafter. The structural formula is shown in Formula 1:

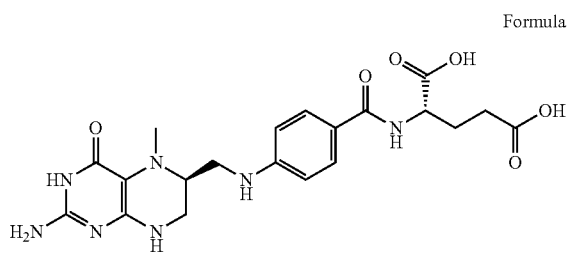

Formula I (6S)-5-MTHF and salts thereof are very unstable and easily degraded, and especially are highly sensitive to oxygen and moisture (A. L. Fitzhugh, Pteridines 1993, 4(4), 187-191). In the air, (6S)-5-MTHF and salts thereof are easily oxidized into 5-methyldihydrofolic acid and/or folic acid and the like. Therefore, it is difficult to prepare high-purity and high-stability bulk pharmaceutical chemicals or food additives, to meet the quality standards.

Due to the physical and chemical properties of (6S)-5-MTHF, it is difficult to prepare a stable crystal form of (6S)-5-MTHF by a conventional crystallization process. In the past few decades of production of (6S)-5-MTHF and preparation of formulations thereof, a reducing agent, for example, Vitamin C or 2-mercaptoethanol, is often added to achieve the purpose of anti-oxidation.

Patent Document U.S. Pat. No. 5,223,500 reports a process for preparing a stable crystal form of (6S)-5-MTHF calcium salt. The process includes the following steps: first, preparing amorphous (6S)-5-MTHF calcium salt, then transferring into boiling water of 100° C. to form a solution, cooling and standing overnight at room temperature. The collected solid is called to be a stable crystal product. However, relevant crystal parameters are not reported in this patent.

Patent Document U.S. Pat. No. 6,441,168 discloses a crystal form of (6S)-5-MTHF calcium salt with extremely high stability and a method for preparing the same. (6S)-5-MTHF sodium salt and calcium chloride are subjected to heat treatment in a polar solvent at about 90° C. to obtain four stable crystal forms of (6S)-5-MTHF calcium salt, which are respectively Form I having 2θ values of 6.3, 13.3, 16.8, and 20.1, Form II having 2θ values of 5.3, 6.9, 5.7, and 21.1, Form III having 2θ values of 6.8, 10.2, 15.4, and 22.5, and Form IV having 2θ values of 6.6, 15.9, 20.2, and 22.5.

Patent Document WO2008144953 discloses a process for preparing a stable amorphous (6S)-5-MTHF calcium salt, in which a crystal form of (6S)-5-MTHF is used as a raw material, calcium chloride is added for slow crystallization. The whole crystallization process in this patent is very complex, and the crystallization time is 16 to 18 hours, thereby reducing the production capacity in the product procedure.

SUMMARY

Surprisingly, it has been found now that by using ultrasonic waves to assist crystallization during the formation of a salt, a crystal form of (6S)-5-methyltetrahydrofolate salt with high stability and good chemical and optical purity can be obtained.

In order to overcome the disadvantages in the prior art, an objective of the present invention is to provide a novel crystal form of (6S)-5-methyltetrahydrofolate salt with good stability, high purity, and good reproducibility.

Preferably, the present invention sets forth Form C of the crystal form of (6S)-5-methyltetrahydrofolate calcium salt, where the X-ray diffraction pattern has diffraction peaks at the 2θ angles of 6.3±0.2 and 19.2±0.2.

Preferably, the present invention sets forth a crystal form of (6S)-5-methyltetrahydrofolate strontium salt, where the X-ray diffraction pattern has diffraction peaks at the 2θ angles of 6.5±0.2 and 22.0±0.2.

Preferably, the X-ray diffraction pattern of the Form C of the crystal form of (6S)-5-methyltetrahydrofolate calcium salt has diffraction peaks at the 2θ angles of 3.2±0.2, 6.3±0.2, 13.2±0.2, 14.6±0.2, 19.2±0.2, and 32.6±0.2.

Preferably, the X-ray diffraction pattern of the crystal form of (6S)-5-methyltetrahydrofolate strontium salt has diffraction peaks at the 2θ angles of 6.5±0.2, 10.0±0.2, 13.7±0.2, 16.8±0.2, 17.1±0.2, 22.0±0.2, and 24.9±0.2.

Preferably, the X-ray diffraction pattern of the Form C of the crystal form of (6S)-5-methyltetrahydrofolate calcium salt has diffraction peaks at the 2θ angles of 3.2±0.1, 6.3±0.1, 13.2±0.1, 14.6±0.1, 19.2±0.1, and 32.6±0.1; or, preferably, the X-ray diffraction pattern of the crystal form of (6S)-5-methyltetrahydrofolate strontium salt has diffraction peaks at the 2θ angles of 6.5±0.1, 10.0±0.1, 13.7±0.1, 16.8±0.1, 17.1±0.1, 22.0±0.1, and 24.9±0.1.

Another objective of the present invention is to provide methods for preparing the crystal form of (6S)-5-methyltetrahydrofolate salt.

The third objective of the present invention is to provide pharmaceutical compositions of the crystal form of (6S)-5-methyltetrahydrofolate salt.

The fourth objective of the present invention is to provide uses of the crystal form of (6S)-5-methyltetrahydrofolate salt.

The objectives of the present invention can be achieved according to the following ways:

A crystal form of (6S)-5-methyltetrahydrofolate salt is provided, where the crystal form is Form C of the crystal form of (6S)-5-methyltetrahydrofolic acid calcium salt or a crystal form of (6S)-5-methyltetrahydrofolate strontium salt.

In an aspect, the present invention provides Form C of the crystal form of (6S)-5-methyltetrahydrofolate calcium salt, where by using Cu-Ka radiation, the X-ray diffraction pattern has diffraction peaks at 2θ of 6.3±0.2 and 19.2±0.2 in degree, especially has one or more diffraction peaks at 2θ of 3.2±0.2, 6.3±0.2, 13.2±0.2, 14.6±0.2, 19.2±0.2, and 32.6±0.2, and preferably has one or more diffraction peaks at 2θ of 3.2±0.1, 6.3±0.1, 13.2±0.1, 14.6±0.1, 19.2±0.1, and 32.6±0.1. The X-ray diffraction pattern of the Form C of the crystal form of (6S)-5-methyltetrahydrofolate calcium salt exhibits strong diffraction peaks and low background spectrum, indicating high crystallinity.

The further X-ray diffraction pattern of the Form C (6S)-5-methyltetrahydrofolic acid calcium salt is essentially shown in FIG. 1. The chemical purity of the Form C of the crystal form of (6S)-5-methyltetrahydrofolate calcium salt is further greater than 99.0%.

In another aspect, the present invention provides a crystal form of (6S)-5-methyltetrahydrofolate strontium salt, where by using Cu-Ka radiation, the X-ray diffraction pattern has diffraction peaks at 2θ of 6.5±0.2 and 22.0±0.2 in degree, especially has one or more diffraction peaks at 2θ of 6.5±0.2, 10.0±0.2, 13.7±0.2, 16.8±0.2, 17.1±0.2, 22.0±0.2, and 24.9±0.2, and preferably has one or more diffraction peaks at 2θ of 6.5±0.1, 10.0±0.1, 13.7±0.1, 16.8±0.1, 17.1±0.1, 22.0±0.1, and 24.9±0.1. The X-ray diffraction pattern of the crystal form of (6S)-5-methyltetrahydrofolate strontium salt exhibits strong diffraction peaks and low background spectrum, indicating high crystallinity.

The further X-ray diffraction pattern of the (6S)-5-methyltetrahydrofolate strontium salt is essentially shown in FIG. 2.

In the present invention, the moisture content of the crystal form of (6S)-5-methyltetrahydrofolate salt is 10% to 18%, and further is 15% to 17%.

In still another aspect, the present invention provides a method for preparing a (6S)-5-methyltetrahydrofolate salt, where the method includes crystallizing (6S)-5-methyltetrahydrofolate salt from a polar medium through ultrasonic assistance.

In yet another aspect, the present invention provides a method for preparing a (6S)-5-methyltetrahydrofolate salt, specifically including the following steps:

(1) Neutralization of (6S)-5-methyltetrahydrofolic acid with a base in a polar medium to full dissolution; the polar medium may be water, deionized water, or a solution formed by water and an organic solvent capable of being mixed uniformly with water, and may also be a salt; a preferred polar medium is water and deionized water. The base is an inorganic base or organic base capable of forming a salt with (6S)-5-methyltetrahydrofolic acid, the inorganic base is selected from alkali metal bases or alkaline earth metal bases, carbonates and bicarbonates; the organic base is selected from ammonia, amines, pyridines or piperazines, where potassium hydroxide, sodium hydroxide, calcium hydroxide, potassium carbonate, sodium carbonate, potassium bicarbonate, sodium bicarbonate, ammonia, methylamine, 4-dimethyl-pyridine or piperazine are preferred.

(2) Addition of an alkaline earth metal salt or an alkaline earth metal salt solution; the alkaline earth metal salt refers to an inorganic salt or organic salt that is soluble or partially solution in the polar medium, for example, calcium salt, magnesium salt, strontium salt, barium salt, and calcium chloride, hexahydrate calcium chloride and strontium chloride are preferred.

(3) Heating to a temperature higher than 30° C., especially to a temperature of 30° C. to 60° C. or 60° C. to 100° C.

(4) Introduction of ultrasonic waves and crystallization, and isolation of (6S)-5-methyltetrahydrofolate salt crystal.

Ultrasonic technology is a simple, inexpensive technique, and is safe and convenient in use. On one hand, ultrasonic wave can strength the nucleation and growth of crystals. In the crystallization process, the introduction of ultrasonic waves may cause cavitation phenomenon, when cavitation bubbles burst, a certain micro-jet is produced, the micro-jet crushes crystal grains having a certain size, and a part of the crushed crystals serve as seed for crystal growth, thereby promoting the growth of crystals. On the other hand, in the crystallization process, ultrasonic waves are equivalent to a catalyst, and excite the molecular motion through translation, rotation and reversal, thereby increasing the crystallization rate of the entire system, and shortening the crystallization time. The ultrasonic waves can also improve the particle size distribution of the product, and with the increase of the ultrasonic power, the crystal particles show a tendency of decrease. Since no other reagents are added and no contaminants are introduced in the crystallization process, the ultrasonic waves can be used to prepare very pure crystalline materials, and this is very important for some materials with very strict requirements for purity, especially pharmaceutical products and foods. Compared with other crystallization starting methods such as stimulation crystallization starting method and seed charging crystallization starting method, the degree of supersaturation required by ultrasonic crystallization is low, the growth speed is fast, the resulting crystal is uniform, complete and clean, the crystal size distribution range is small, and the coefficient of variation is low.

Ultrasonic waves have been used in crystalline area since 1927. In recent years, the utilization of ultrasonic waves in pharmaceutical and fine chemical industries is further promoted. Ishtiaq et al. reviewed the application of ultrasonic waves in the pharmaceutical field (World Applied sciences Journal (2009), 6(7), 856-893). However, so far, in the pharmaceutical industry, merely several papers and patents disclose and apply the ultrasonic crystallization technique, for example, paroxetine, aspartame, adipic acid, fenoterol hydrobromide (Organic Process Research & Development 2005, 9, 923-932).

The inventors apply ultrasonic waves in the field of crystallization of 5-methyltetrahydrofolic acid and salts thereof for the first time. We have found in experiments that when the ultrasonic power is 0.01 W/ml to 1.0 W/ml, the resulting crystal is uniform, complete, and clean, the crystal size distribution range is small, and the purity is high and is up to above 99.0%. Preferably, the ultrasonic power is 0.04 W/ml to 0.60 W/ml.

Neutralization with a base in Step (1) generally refers to neutralization to a pH value of about 7.0, generally neutralization to a pH value of 6.5 to 8.5, preferably neutralization to a pH value of 7.0 to 7.5, and most preferably neutralization to a pH value of 7.0. The base may be directly added, and may also be added in the form of a solution (for example, aqueous solution). This method has not specific requirements on the amount of the polar medium, and an amount for a general reaction or a crystallization medium is suitable.

When an alkaline earth metal salt solution is used in Step (2), generally a 5% to 50% aqueous solution of an alkaline earth metal salt, preferably a 25% to 50% aqueous solution of an alkaline earth metal salt, is used.

The heating temperature in Step (3) is 30° C. to 60° C. or 60° C. to 100° C., preferably 40° C. to 80° C., and more preferably 65° C. to 70° C.

In Step (4), after ultrasonic crystallization and isolation the crystal, a step of washing with water and drying (drying in vacuum at a temperature of 20° C. to 40° C.).

Preparation of the crystal form of (6S)-5-methyltetrahydrofolate salt by using ultrasonic waves can be carried out naturally or be carried out by introducing a corresponding (6S)-5-methyltetrahydrofolate salt seed.

In another aspect, the present invention relates to a composition containing at least one (6S)-5-methyltetrahydrofolate salt described above, since persons skilled in the art can understand based on the knowledge in the art that the composition of the present invention may further contain a pharmaceutically acceptable excipient or carrier. The carrier includes a diluent, a binder, a disintegrant, a lubricant, and an anti-oxidant, and these excipients are existing conventional excipients. The preparation form of the composition is an oral solid preparation or injection, for example, tablets, capsules, orally disintegrating tablets, lozenge, sustained-release preparations, injections, and lyophilized powder, prepared by adopting methods for corresponding formulations.

A preparation is provided, which contains an effective amount of the crystal form of (6S)-5-methyltetrahydrofolate salt.

In another aspect, the present invention discloses a use of the at least one (6S)-5-methyltetrahydrofolate salt and/or composition defined above in preparation of pharmaceuticals, food additives or nutritional supplements, where the pharmaceuticals, food additives, or nutritional supplements are used for preventing and/or treating defects or diseases positively impacted by administration of 5-methyltetrahydrofolate salt.

Merely for example, the (6S)-5-methyltetrahydrofolate salt and/or composition of the present invention defined above may be used in preparation of pharmaceuticals, food additives, or nutritional supplements. The pharmaceuticals, food additives, or nutritional supplements are used for preventing and/or treating neurological diseases such as subacute encephali associated with dementia and vacuolar myelopathy; physiological and pathological vascular and cardiovascular disorders such as premature occlusive arterial diseases, severe vascular diseases in infancy and childhood, progressive arterial stenosis, intermittent claudication, renal vascular hypertension, ischemic cerebrovascular diseases, premature occlusive retinal artery and retinal vein, cerebral occlusive arterial diseases, occlusive peripheral arterial diseases, and premature death caused by thromboembolic diseases and/or ischemic heart diseases; autoimmune diseases such as psoriasis, celiac disease, arthritis and inflammatory conditions; megaloblastic anemia caused by folate inefficiency, intestinal malabsorption, used as antidote for folic acid antagonists (for example, methotrexate, pyrimethamine or trimethoprim); used for preventing serious toxic effects caused by methotrexate overdose or high-dose therapy, reducing risks of woman miscarriage and/or production of fetuses with neural tube defects, cleft defects and/or palate defects, keeping and/or normalizing homocysteine levels and/or metabolism; changes synthesis of and/or functions and/or variations in DNA and RNA and changes in synthesis of cells; and depression.

The (6S)-5-methyltetrahydrofolate salt of the present invention exhibits long-term persistent chemical stability, and after long-term exposure in the air at a temperature of 40° C. and relative humidity of 60%, and the color of the crystal form has no significant changes, which is very important for application of the (6S)-5-methyltetrahydrofolate salt in pharmaceutical preparations.

In addition to the rare high chemical stability, it may also be noted that, the (6S)-5-methyltetrahydrofolate salt of the present invention has good dissolution rate, and in water at a temperature of 25° C., the saturated state can be quickly reached within 1 min. The high dissolution rate can not only improve the producibility of preparations for parenteral administration such as injections, thereby facilitating industrial production, and can also be made into oral preparations, thereby having important biopharmaceutical advantages in oral administration of pharmaceuticals, because the high dissolution rate of the active pharmaceuticals improves the absorption rate of the active pharmaceuticals through the gastrointestinal wall. Additionally, the crystal form of the present invention further has the advantages of high crystallinity, uniform particle distribution, smooth surface, and high chemical purity of up to above 99.0%.

The method for preparing the crystal form of (6S)-5-methyltetrahydrofolate salt of the present invention has the advantages that the reaction steps are simple, no pollution occurs, the obtained novel crystal form of (6S)-5-methyltetrahydrofolic acid calcium salt has high chemical stability, high purity, high dissolution rate, and high bioavailability, thereby providing a novel way for preparing (6S)-5-methyltetrahydrofolate crystalline salt.

The crystal form of (6S)-5-methyltetrahydrofolate salt of the present invention has the advantages of excellent physicochemical properties, good stability, high purity, good reproducibility, and being more suitable for production on an industrial scale.

BRIEF DESCRIPTION OF DRAWINGS

The disclosure will become more fully understood from the detailed description given herein below for illustration only, and thus are not limitative of the disclosure, and wherein.

DETAILED DESCRIPTION

Figure 1:
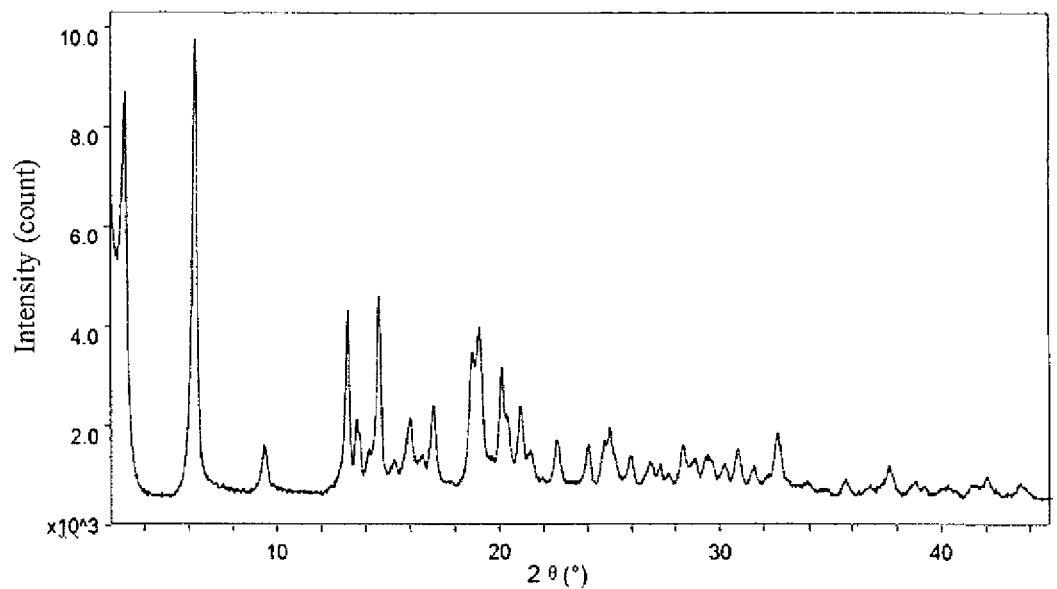
FIG. 1 shows an X-ray diffraction pattern of Form C of the crystal form of (6S)-5-methyltetrahydrofolate calcium salt.

Without further description, by means of the previous description, persons skilled in the art can implement the present invention to the maximum. The following preferred specific embodiments are just examples, and in no way limit the disclosure of the present invention.

Embodiment 1

15.0 g (6S)-5-MTHF was added to 325 ml deionized water, and 10% NaOH solution was added with stirring for neutralization to a pH value of 7.8 till (6S)-5-MTHF was fully dissolved. Next, 37.5 g calcium chloride solution (containing 9.0 g calcium chloride) was added, the resulting reaction solution was transferred into an ultrasonic reactor having a power density of 0.04 W/ml at a temperature of 72° C., and after 40 min-ultrasonic reaction, the reaction solution was filtered, and washed with water, ethanol and acetone respectively. After drying in vacuum at 25° C., 13.5 g white Form C of (6S)-5-MTHF calcium salt was obtained. The chemical purity is 99.25% (detected by HPLC), and the moisture content is 10.67%.

Embodiment 2

10.0 g (6S)-5-MTHF was added to 250 ml water, and 10% NaOH solution was added with stirring for neutralization to a pH value of 7.4 till (6S)-5-MTHF was fully dissolved. Next, 25 g calcium chloride solution (containing 6.0 g calcium chloride) was added, the resulting reaction solution was transferred into an ultrasonic reactor having a power density of 0.03 W/ml at a temperature of 60° C., and after 40 min-ultrasonic reaction, the reaction solution was filtered, and washed with water and acetone. After drying in vacuum at 30° C., 9.2 g white Form C of (6S)-5-MTHF calcium salt was obtained. The chemical purity is 99.01% (detected by HPLC), and the moisture content is 15.8%.

Embodiment 3

10.0 g (6S)-5-MTHF was added to 150 ml water, and ammonia was added with stirring for neutralization to a pH value of 7.4 till (6S)-5-MTHF was fully dissolved. Next, 12 g calcium chloride solution (containing 3.0 g calcium chloride) was added, the resulting reaction solution was transferred into an ultrasonic reactor having a power density of 0.05 W/ml at a temperature of 40° C., and after 100 min-ultrasonic reaction, the reaction solution was filtered, and washed with water and acetone. After drying in vacuum at 25° C., 9.0 g white Form C of (6S)-5-MTHF calcium salt was obtained. The chemical purity is 99.60% (detected by HPLC), and the moisture content is 17.76%.

Embodiment 4

40.0 g (6S)-5-MTHF was added to 1,000 ml water, and 10% NaOH solution was added with stirring for neutralization to a pH value of 7.8 till (6S)-5-MTHF was fully dissolved. Next, 96 g calcium chloride solution (containing 24 g calcium chloride) was added, the resulting reaction solution was transferred into an ultrasonic reactor having a power density of 0.56 W/ml at a temperature of 90° C., and after 30 min-ultrasonic reaction, the reaction solution was filtered, and washed with water and acetone. After drying in vacuum at 25° C., 36.0 g white Form C of (6S)-5-MTHF calcium salt was obtained. The chemical purity is 99.77% (detected by HPLC), and the moisture content is 16.39%.

Embodiment 5

Strontium Salt 6.0 g (6S)-5-MTHF was added to 150 ml water, and 10% NaOH solution was added with stirring for neutralization to a pH value of 7.3 till (6S)-5-MTHF was fully dissolved. Next, 7.29 g strontium chloride solution (containing 1.8 g strontium chloride) was added, the resulting reaction solution was transferred into an ultrasonic reactor having a power density of 0.30 W/ml at a temperature of 70° C., and after 20 min-ultrasonic reaction, the reaction solution was filtered, and washed with water and acetone. After drying in vacuum at 25° C., 4.2 g white (6S)-5-MTHF strontium salt was obtained. The chemical purity is 97.57% (detected by HPLC), and the moisture content is 15.02%.

Embodiment 6

9.0 g (6S)-5-MTHF was added to 225 ml water, and 10% NaOH solution was added with stirring for neutralization to a pH value of 7.1 till (6S)-5-MTHF was fully dissolved. Next, 10.2 g calcium chloride solution (containing 2.7 g calcium chloride) was added, the resulting reaction solution was transferred into an ultrasonic reactor having a power density of 0.20 W/ml at a temperature of 70° C., and after 20 min-ultrasonic reaction, the reaction solution was filtered, and washed with water and acetone. After drying in vacuum at 25° C., 6.1 g white Form C of (6S)-5-MTHF calcium salt was obtained. The chemical purity is 99.08% (detected by HPLC), and the moisture content is 15.20%.

Embodiment 7

18.0 g (6S)-5-MTHF was added to 450 ml water, and 10% NaOH solution was added with stirring for neutralization to a pH value of 7.3 till (6S)-5-MTHF was fully dissolved. Next, 21.6 g calcium chloride solution (containing 5.4 g calcium chloride) was added, the resulting reaction solution was transferred into an ultrasonic reactor having a power density of 0.04 W/ml at a temperature of 70° C., and after 30 min-ultrasonic reaction, the reaction solution was filtered, and washed with water and acetone. After drying in vacuum at 25° C., 13.9 g white Form C of (6S)-5-MTHF calcium salt was obtained. The chemical purity is 99.53% (detected by HPLC), and the moisture content is 16.4%.

Embodiment 8

2.0 g (6S)-5-MTHF was added to 50 ml water, and sodium hydroxide was added with stirring for neutralization to a pH value of 7.2 till (6S)-5-MTHF was fully dissolved. Next, 2 g calcium chloride solution (containing 0.5 g calcium chloride) was added, the resulting reaction solution was transferred into an ultrasonic reactor having a power density of 0.05 W/ml at a temperature of 50° C., and after 60 min-ultrasonic reaction, the reaction solution was filtered, and washed with water and acetone. After drying in vacuum at 40° C., 1.0 g white Form C of (6S)-5-MTHF calcium salt was obtained. The chemical purity is 99.01% (detected by HPLC), and the moisture content is 15.6%.

Although the above specific embodiments merely disclose the preparation methods of the (6S)-5-methyltetrahydrofolic acid calcium salt crystal and the (6S)-5-methyltetrahydrofolate strontium salt crystal, persons skilled in the art can prepare other types of (6S)-5-methyltetrahydrofolate salt crystals according to the teaching of the preparation methods, particularly the (6S)-5-methyltetrahydrofolic acid alkaline earth metal salt crystals.

Embodiment 9

Stability Study

In order to determine the stability of the novel crystal form of the Form C of (6S)-5-MTHF calcium salt, the crystal form was placed in the air at a temperature of 40° C. and a relative humidity of 60%, and the content of remained (6S)-5-MTHF calcium salt was periodically measured.

| Crystal Form | Storage Days | Appearance | Content |
|---|---|---|---|
| Form C | 0 | White crystal | 99.5% |
| | 3 | White crystal | 99.1% |
| | 6 | White crystal | 99.1% |
| | 9 | White crystal | 98.4% |

The results show that the Form C of (6S)-5-MTHF calcium salt has good stability, which is beneficial to the production and storage of pharmaceutical preparations.

Embodiment 10

Figure 3:
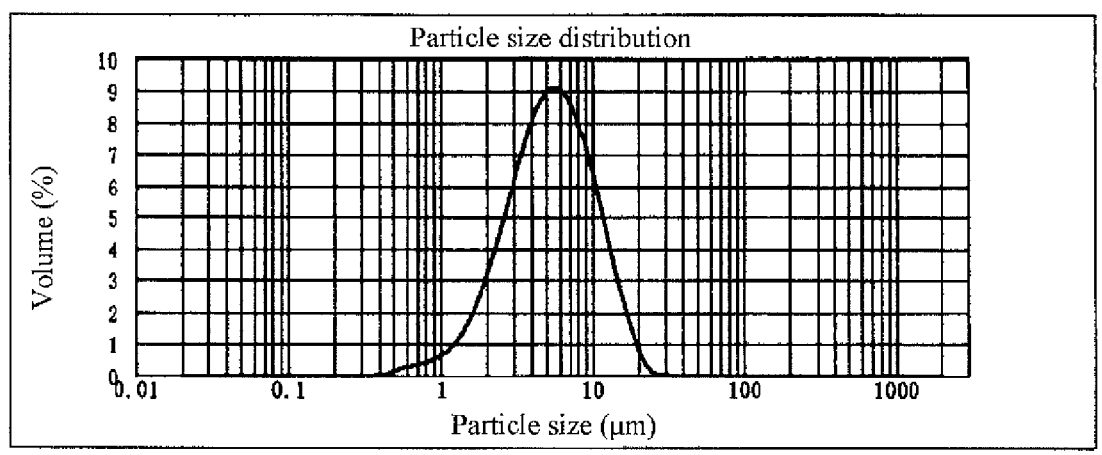
FIG. 3 shows the particle diameter distribution of Form C of the crystal form of (6S)-5-methyltetrahydrofolate calcium salt obtained through the preparation method of the present invention.

Particle Diameter Distribution of the Form C of the Crystal Form of (6S)-5-Methyltetrahydrofolate Calcium Salt FIG. 3 shows the particle diameter distribution of the Form C of the crystal form of (6S)-5-methyltetrahydrofolate calcium salt obtained through the preparation method of the present invention. It can be seen from FIG. 3 that, the particle size is in normal distribution, indicating that the crystal treated by ultrasonic waves has a relatively uniform particle size.

Embodiment 11

Conditions and Data of the X-Ray Diffraction Pattern of the Crystal Form

Instrument: Bruker DS advance XRD
Diffraction ray: CuKα (40 kV, 40 mA)
Scanning rate: 80°/min (2θ value)
Scanning range: 2° to 45° (2θ value)
Peak Search Report (37 Peaks, Max P/N=46.1)
PEAK: 35-pts/Parabolic Filter, Threshold=3.0, Cut-off=0.1%, BG=3/1.0, Peak–Top=Sumnmit

| # | 2-Theta | d(A) | BG | Height | I % | Area | I % | FWHM |
|---|---|---|---|---|---|---|---|---|
| 1 | 3.151 | 28.0163 | 612 | 8740 | 89.06 | 165950 | 100.00 | 0.343 |
| 2 | 6.309 | 13.9974 | 689 | 9814 | 100.00 | 155754 | 93.86 | 0.286 |
| 3 | 9.447 | 9.3545 | 681 | 1601 | 16.31 | 16953 | 10.22 | 0.309 |
| 4 | 13.199 | 6.7022 | 913 | 4338 | 44.20 | 46545 | 28.05 | 0.228 |
| 5 | 13.612 | 6.4999 | 1029 | 2121 | 21.61 | 14775 | 8.90 | 0.227 |
| 6 | 14.166 | 6.2469 | 1072 | 1514 | 15.43 | 12344 | 7.44 | 0.441 |
| 7 | 14.639 | 6.0462 | 1057 | 4630 | 47.18 | 52370 | 31.56 | 0.246 |
| 8 | 15.329 | 5.7755 | 1055 | 1310 | 13.35 | 2233 | 1.35 | 0.147 |
| 9 | 16.001 | 5.5343 | 1133 | 2147 | 21.88 | 18187 | 10.96 | 0.301 |
| 10 | 16.534 | 5.3572 | 958 | 1409 | 14.36 | 15394 | 9.28 | 0.539 |
| 11 | 17.046 | 5.1973 | 1089 | 2406 | 24.52 | 14700 | 8.86 | 0.187 |
| 12 | 18.824 | 4.7103 | 1017 | 3484 | 35.50 | 74762 | 45.05 | 0.479 |
| 13 | 19.158 | 4.6288 | 1118 | 3998 | 40.74 | 84209 | 50.74 | 0.491 |
| 14 | 20.125 | 4.4085 | 1295 | 3176 | 32.36 | 30820 | 18.57 | 0.275 |
| 15 | 20.976 | 4.2316 | 1169 | 2397 | 24.42 | 22579 | 13.61 | 0.308 |
| 16 | 21.411 | 4.1466 | 1068 | 1503 | 15.31 | 5525 | 3.33 | 0.213 |
| 17 | 22.614 | 3.9287 | 863 | 1716 | 17.49 | 13799 | 8.32 | 0.271 |
| 18 | 24.073 | 3.6937 | 857 | 1619 | 16.50 | 9785 | 5.90 | 0.215 |
| 19 | 24.785 | 3.5892 | 884 | 1719 | 17.52 | 26584 | 16.02 | 0.503 |
| 20 | 25.022 | 3.5558 | 898 | 1971 | 20.08 | 26647 | 16.06 | 0.417 |
| 21 | 25.914 | 3.4354 | 884 | 1390 | 14.16 | 7075 | 4.26 | 0.235 |
| 22 | 26.858 | 3.3168 | 846 | 1262 | 12.86 | 10476 | 6.31 | 0.423 |
| 23 | 27.334 | 3.2601 | 852 | 1244 | 12.68 | 8923 | 5.38 | 0.359 |
| 24 | 27.674 | 3.2207 | 901 | 1048 | 10.68 | 1050 | 0.63 | 0.113 |
| 25 | 28.358 | 3.1446 | 915 | 1606 | 16.36 | 15814 | 9.53 | 0.384 |
| 26 | 28.908 | 3.0860 | 913 | 1339 | 13.64 | 16265 | 9.80 | 0.641 |
| 27 | 29.444 | 3.0310 | 977 | 1419 | 14.46 | 9424 | 5.68 | 0.358 |
| 28 | 30.251 | 2.9520 | 921 | 1248 | 12.72 | 3742 | 2.25 | 0.192 |
| 29 | 30.769 | 2.9035 | 880 | 1518 | 15.47 | 9728 | 5.86 | 0.256 |
| 30 | 31.537 | 2.8345 | 836 | 1196 | 12.19 | 4349 | 2.62 | 0.203 |
| 31 | 32.602 | 2.7443 | 813 | 1863 | 18.98 | 21721 | 13.09 | 0.347 |
| 32 | 35.722 | 2.5115 | 617 | 929 | 9.47 | 4980 | 3.00 | 0.268 |
| 33 | 37.675 | 2.3856 | 659 | 1229 | 12.52 | 10784 | 6.50 | 0.317 |
| 34 | 38.819 | 2.3179 | 633 | 884 | 9.01 | 5939 | 3.58 | 0.397 |
| 35 | 40.263 | 2.2381 | 607 | 776 | 7.91 | 4592 | 2.77 | 0.429 |
| 36 | 42.037 | 2.1476 | 580 | 988 | 10.07 | 14181 | 8.55 | 0.583 |
| 37 | 43.615 | 2.0735 | 563 | 841 | 8.57 | 6633 | 4.00 | 0.400 |

Embodiment 12

Conditions and Data of the X-Ray Diffraction Pattern of the Crystal Form of Strontium Salt Instrument model: Bruker D8 advance XRD
Diffraction ray: CuKα (40 kv, 40 mA)
Scanning rate: 8°/min (2θ value)
Scanning range: 5° to 45° (2θ value)
Peak Search Report (36 Peaks, Max P/N=20.9)
PEAK: 29-pts/Parabolic Filter, Threshold=3.0, Cut-off=0.1%, BG=3/1.0, Peak–Top=Summit

| # | 2-Theta | d(A) | BG | Height | I % | Area | I % | FWHM |
|---|---|---|---|---|---|---|---|---|
| 1 | 6.54 | 13.503 | 581 | 2213 | 100 | 46131 | 100 | 0.354 |
| 2 | 7.496 | 11.7831 | 565 | 96 | 4.3 | 1563 | 3.4 | 0.277 |
| 3 | 8.38 | 10.5426 | 570 | 136 | 6.1 | 2418 | 5.2 | 0.302 |

-continued

| # | 2-Theta | d(A) | BG | Height | I % | Area | I % | FWHM |
|---|---------|------|-----|--------|------|-------|------|-------|
| 4 | 9.96 | 8.8736 | 610 | 1379 | 62.3 | 35198 | 76.3 | 0.434 |
| 5 | 12.339 | 7.1672 | 647 | 292 | 13.2 | 5831 | 12.6 | 0.339 |
| 6 | 13.66 | 6.4772 | 902 | 604 | 27.3 | 20626 | 44.7 | 0.581 |
| 7 | 14.22 | 6.2232 | 826 | 413 | 18.7 | 26525 | 57.5 | 1.092 |
| 8 | 14.741 | 6.0044 | 940 | 355 | 16 | 5431 | 11.8 | 0.26 |
| 9 | 15.58 | 5.6828 | 842 | 199 | 9 | 3770 | 8.2 | 0.322 |
| 10 | 16.279 | 5.4403 | 1049 | 239 | 10.8 | 2625 | 5.7 | 0.187 |
| 11 | 16.8 | 5.2729 | 815 | 533 | 24.1 | 28957 | 62.8 | 0.924 |
| 12 | 17.14 | 5.169 | 898 | 672 | 30.4 | 16152 | 35 | 0.409 |
| 13 | 18.28 | 4.8492 | 796 | 664 | 30 | 16290 | 35.3 | 0.417 |
| 14 | 19.54 | 4.5393 | 819 | 598 | 27 | 15788 | 34.2 | 0.449 |
| 15 | 20.3 | 4.371 | 779 | 328 | 14.8 | 5046 | 10.9 | 0.262 |
| 16 | 22.02 | 4.0334 | 699 | 1281 | 57.9 | 31787 | 68.9 | 0.422 |
| 17 | 23.259 | 3.8211 | 764 | 131 | 5.9 | 2094 | 4.5 | 0.272 |
| 18 | 24.399 | 3.6451 | 944 | 589 | 26.6 | 22484 | 48.7 | 0.649 |
| 19 | 24.92 | 3.5702 | 911 | 788 | 35.6 | 34957 | 75.8 | 0.754 |
| 20 | 26.42 | 3.3707 | 830 | 673 | 30.4 | 12784 | 27.7 | 0.323 |
| 21 | 27.999 | 3.1841 | 838 | 310 | 14 | 5810 | 12.6 | 0.319 |
| 22 | 28.961 | 3.0805 | 851 | 249 | 11.3 | 4360 | 9.5 | 0.298 |
| 23 | 29.881 | 2.9877 | 723 | 138 | 6.2 | 2168 | 4.7 | 0.267 |
| 24 | 30.84 | 2.897 | 679 | 190 | 8.6 | 3775 | 8.2 | 0.338 |
| 25 | 32.04 | 2.7912 | 678 | 220 | 9.9 | 7951 | 17.2 | 0.614 |
| 26 | 32.44 | 2.7577 | 683 | 157 | 7.1 | 7115 | 15.4 | 0.77 |
| 27 | 33.12 | 2.7026 | 662 | 190 | 8.6 | 2851 | 6.2 | 0.255 |
| 28 | 34.12 | 2.6256 | 655 | 149 | 6.7 | 4534 | 9.8 | 0.517 |
| 29 | 35.041 | 2.5587 | 674 | 88 | 4 | 2007 | 4.4 | 0.388 |
| 30 | 37.179 | 2.4163 | 663 | 223 | 10.1 | 8948 | 19.4 | 0.682 |
| 31 | 37.723 | 2.3827 | 689 | 142 | 6.4 | 7683 | 16.7 | 0.92 |
| 32 | 39.78 | 2.2641 | 592 | 373 | 16.9 | 9421 | 20.4 | 0.429 |
| 33 | 41.019 | 2.1985 | 577 | 122 | 5.5 | 3827 | 8.3 | 0.533 |
| 34 | 42.84 | 2.1092 | 648 | 445 | 20.1 | 17304 | 37.5 | 0.661 |
| 35 | 43.298 | 2.0879 | 726 | 211 | 9.5 | 10128 | 22 | 0.816 |
| 36 | 44.321 | 2.0421 | 683 | 153 | 6.9 | 4026 | 8.7 | 0.447 |

Therefore, the present invention relates to the crystal form of (6S)-5-methyltetrahydrofolate salt prepared by the above method.

The crystal form of (6S)-5-methyltetrahydrofolate salt is:

(a) Form C of the crystal form of (6S)-5-methyltetrahydrofolate calcium salt, where the X-ray diffraction pattern has diffraction peaks at the 2θ angles of 6.3±0.2 and 19.2±0.2; or (b) Crystal form of (6S)-5-methyltetrahydrofolate strontium salt, where the X-ray diffraction pattern has diffraction peaks at the 2θ angles of 6.5±0.2 and 22.0±0.2.

Preferably, the crystal form of (6S)-5-methyltetrahydrofolate salt is:

(a) Form C of the crystal form of (6S)-5-methyltetrahydrofolate calcium salt, where the X-ray diffraction pattern has diffraction peaks at the 2θ angles of 3.2±0.2, 6.3±0.2, 13.2±0.2, 14.6±0.2, 19.2±0.2 and 32.6±0.2; or (b) the crystal form of (6S)-5-methyltetrahydrofolate strontium salt, where the X-ray diffraction pattern has diffraction peaks at the 2θ angles of 6.5±0.2, 10.0±0.2, 13.7±0.2, 16.8±0.2, 17.1±0.2, 22.0±0.2 and 24.9±0.2.

Preferably, the crystal form of (6S)-5-methyltetrahydrofolate salt is:

(a) Form C of the crystal form of (6S)-5-methyltetrahydrofolate calcium salt, where the X-ray diffraction pattern has diffraction peaks at the 2θ angles of 3.2±0.1, 6.3±0.1, 13.2±0.1, 14.6±0.1, 19.2±0.1 and 32.6±0.1; or (b) the crystal form of (6S)-5-methyltetrahydrofolate strontium salt, where the X-ray diffraction pattern has diffraction peaks at the 2θ angles of 6.5±0.1, 10.0±0.1, 13.7±0.1, 16.8±0.1, 17.1±0.1, 22.0±0.1 and 24.9±0.1.

Figure 2:
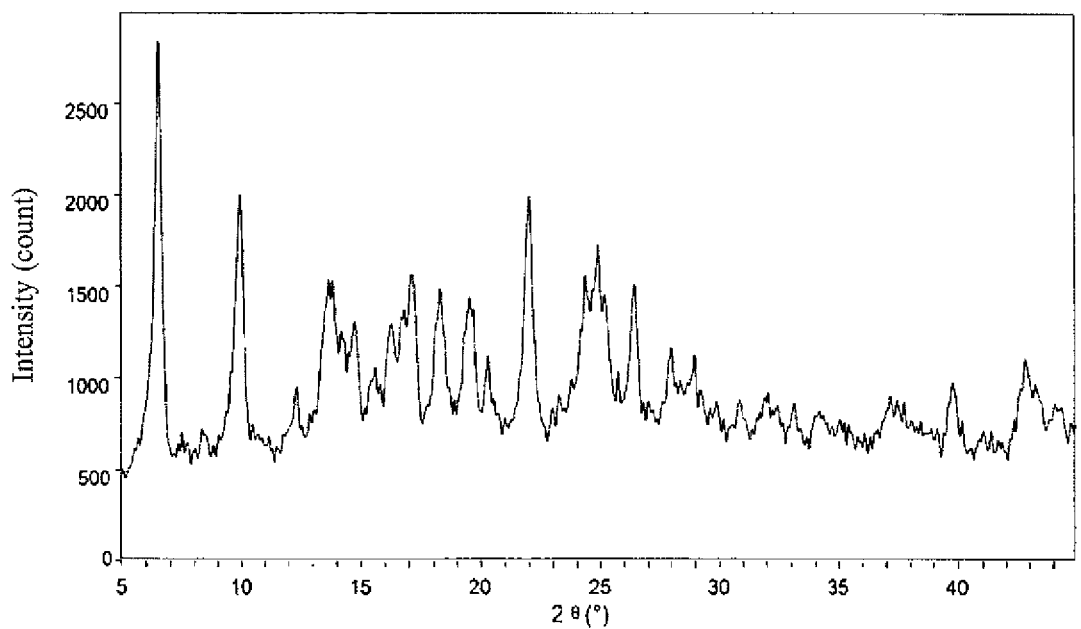
FIG. 2 shows an X-ray diffraction pattern of the crystal form of (6S)-5-methyltetrahydrofolate strontium salt.

Specifically, the crystal form of (6S)-5-methyltetrahydrofolate salt is:

(a) X-ray diffraction pattern of the Form C of the crystal form of (6S)-5-methyltetrahydrofolate calcium salt is essentially shown in FIG. 1; or (b) X-ray diffraction pattern of the crystal form of (6S)-5-methyltetrahydrofolate strontium salt is essentially shown in FIG. 2.

The preferred or specific embodiments of the present invention are described above in detail. It should be understood that persons skilled in the art can make various modifications and variations according to the design concept of the present invention without any creative work. Therefore, all technical solutions that can be obtained by persons skilled in the art through logical analysis, reasoning or limited experiments based on the prior art according to the design concept of the present invention shall fall within the scope of the present invention and/or the protection scope defined by the claims.

What is claimed is:

1. A crystal form of (6S)-5-methyltetrahydrofolate salt, wherein the crystal form is:

(a) Form C of the crystal form of (6S)-5-methyltetrahydrofolate calcium salt, wherein the X-ray diffraction pattern has diffraction peaks at the 2θ angles of 3.2±0.2, 6.3±0.2, 13.2±0.2, 14.6±0.2, 19.2±0.2 and 32.6±0.2.

2. A method for preparing Form C of the crystal form of (6S)-5-methyltetrahydrofolate calcium salt having diffraction peaks at the 2θ angles of 3.2±0.2, 6.3±0.2, 13.2±0.2, 14.6±0.2, 19.2±0.2 and 32.6±0.2, wherein the Form C of (6S)-5-methyltetrahydrofolate calcium salt is crystallized from a polar medium, wherein the crystallization process comprises:

a) adding (6S)-5-methyltetrahydrofolic acid to a polar medium and neutralizing with a base;

b) adding a calcium salt or a solution of a calcium salt;

c) heating to a temperature in the range of 30° C. to 60° C. or 60° C. to 100° C.; and d) introducing ultrasonic waves for crystallization, and e) isolating the Form C of (6S)-5-methyltetrahydrofolate calcium salt.

3. The method according to claim 2, wherein the crystallization process is carried out at a temperature in the range of 30° C. to 60° C. or 60° C. to 100° C.

4. The method according to claim 2, wherein the polar medium in Step a) is water, deionized water or a solution formed by water and an organic solvent capable of being mixed uniformly with water.

5. The method according to claim 2, wherein the base in Step a) is selected from potassium hydroxide, sodium hydroxide, calcium hydroxide, potassium carbonate, sodium carbonate, potassium bicarbonate, sodium bicarbonate, ammonia, methylamine, 4-dimethyl-pyridine or piperazine.

6. The method according to claim 2, wherein the ultrasonic power density is 0.01 w/ml to 1.0 w/ml.

7. The method according to claim 6, wherein the ultrasonic power density is 0.04 w/ml to 0.60 w/ml.

8. A pharmaceutical composition, comprising the Form C crystal form of (6S)-5-methyltetrahydrofolate calcium salt according to claim 1 as a main active ingredient and at least a pharmaceutically acceptable excipient.

* * * * *